United States Patent [19]

Johnston

[11] 4,330,321

[45] May 18, 1982

[54] COMPOUNDS AND METHOD FOR SELECTIVELY CONTROLLING GRASSY WEEDS IN BROADLEAVED CROPS

[75] Inventor: Howard Johnston, Walnut Creek, Calif.

[73] Assignee: The Dow Chemical Company, Midland, Mich.

[21] Appl. No.: 244,374

[22] Filed: Mar. 16, 1981

[51] Int. Cl.³ .................... C07D 213/64; A01N 43/40
[52] U.S. Cl. ......................................... 71/94; 546/291
[58] Field of Search ............................ 546/291; 71/94

[56] References Cited

U.S. PATENT DOCUMENTS

| | | | |
|---|---|---|---|
| 3,931,200 | 1/1976 | Gulbenk | 546/305 |
| 3,931,201 | 1/1976 | Gulbenk | 546/291 |
| 3,962,265 | 6/1976 | Johnston | 546/291 |
| 4,213,774 | 7/1980 | Schurter et al. | 71/94 |
| 4,243,410 | 1/1981 | Bohner et al. | 71/118 |

Primary Examiner—Alan L. Rotman

[57] ABSTRACT

Novel N-alkylaminocarbonyl-2-(4-((3-halo-5-(trifluoromethyl)-2-pyridinyl)oxy)phenoxy)propanamides provide selective control of grassy weeds in the presence of valuable crops.

9 Claims, No Drawings

COMPOUNDS AND METHOD FOR SELECTIVELY CONTROLLING GRASSY WEEDS IN BROADLEAVED CROPS

BACKGROUND OF THE INVENTION

Belgian Pat. No. 868,875 to Ishihara Sangyo Kaisha Ltd. discloses and claims a number of 4-(5-trifluoromethyl-2-pyridyloxy)phenoxy alkanoic acids and their derivatives as well as their use as herbicides in broad-leaved crops.

British Pat. No. 1,550,574 to Ciba Geigy AG discloses and claims a number of pyridyloxphenoxy propionic acid compounds and their herbicidal use. This reference teaches the use of such compounds as plant growth regulators, as for controlling tobacco sucker growth.

Other pyridyloxyphenoxy propionic acid products and methods are disclosed in copending application Ser. No. 817,943 filed July 22, 1977 corresponding to European Patent Application 483 and in copending applications PCT/US 80/00956 and PCT/US 80/01018 filed July 30, 1980.

U.S. Pat. No. 3,816,092, issued June 11, 1974, teaches the selective control of weeds in a variety of crops, including rice. This reference teaches at Col. 1, lines 42–45, that herbicidally active agents cannot be predicted from the prior knowledge of compounds that have herbicidal activity.

The principal weed of rice is an annual grass, *Echinochloa crusgalli*. This grass and its close relatives are troublesome weeds in many countries of the world. Although a number of chemicals and techniques have been developed to attack this problem, there has not yet been a completely acceptable method for controlling such grassy weeds in the presence of desirable crops such as rice.

SUMMARY OF THE INVENTION

This invention provides novel compounds having the formula:

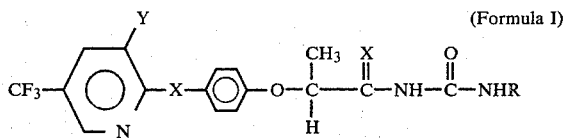

(Formula I)

wherein Y is hydrogen, chloro or bromo; X is O or S, and R is an alkyl or chlorosubstituted alkyl radical having from 1 to 6 carbon atoms.

The compounds of the above formula have been found to be especially active as herbicides for the control of undesired vegetation, for example, grassy or graminaceous weeds.

The invention also provides a method for selectively controlling grassy weeds in the presence of broadleaved crops which comprises applying to the weeds at least a herbicidally effective amount, but less than an amount which is phytotoxic to the crops, of a compound of Formula I as set forth hereinabove.

DETAILED DESCRIPTION OF THE INVENTION

The compounds employed in the method of the present invention are novel compounds and may be prepared using the requisite starting materials by the methods illustrated in the following Examples I and II.

In the general procedure, an appropriate pyridyloxyphenoxypropanamide (1.0 mole) is dissolved in an anhydrous solvent and the desired isocyanate (3.0 moles) added. The reaction mixture is then refluxed for 4 to 16, preferably 12 to 16 hours after which the solvent is removed and the product purified, usually by treatment with decolorizing carbon followed by crystallization. Suitable solvents include, for example, hexane, heptane, toluene, acetonitrile and various alcohols.

EXAMPLE I

N-((Butylamino)carbonyl)-2-(4-((3-chloro-5-(trifluoromethyl)-2-pyridyl)oxy)phenoxy)-propanamide

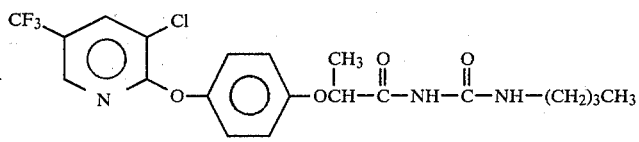

2-(4-((3-Chloro-5-(trifluoromethyl)-2-pyridyl)-oxy)-phenoxy)propanamide (2.24 grams (g), 0.006 mole) was dissolved in dry toluene (50 ml). Butyl isocyanate (1.8 g, 0.018 mole) was then added and the mixture refluxed 13 hours. At the end of this time most of the toluene was removed by distillation under reduced pressure and the residue taken up in hot heptane and treated with decolorizing carbon. After filtration and cooling the product was deposited in the form of fine white crystals, m.p. 126°–127° C.; Yield 2.1 g; 73.6%.

| Analysis: | C | H | N | Cl |
| --- | --- | --- | --- | --- |
| Found | 52.2 | 4.66 | 9.24 | 7.94 |
| Calculated | 52.23 | 4.50 | 9.13 | 7.71 |

EXAMPLE II

N((Isopropylamino)carbonyl)-2-(4-((3-chloro-5-(trifluoromethyl)-2-pyridyl)-oxy)phenoxy)propanamide 2-(4-((3-Chloro-5-(trifluoromethyl)-2-pyridyl)-oxy)-phenoxy)propanamide (3.6 g, 0.01 mole) was dissolved in 80 ml. dry toluene. Isopropyl isocyanate (2.55 g, 0.03 mole) was then added and the mixture refluxed for about 16 hours. The toluene was removed by distillation and cold hexane was added. The product precipitated as white crystals, m.p. 135°–137° C.; Yield 3.6 g; 80.7%.

| Analysis: | C | H | N | Cl |
| --- | --- | --- | --- | --- |
| Found | 50.91 | 4.29 | 8.03 | 9.39 |
| Calculated | 51.18 | 4.29 | 7.95 | 9.42 |

Employing the above procedures the following compounds were prepared: (In all cases X=O and Y=Cl)

| R | m.p. °C. | | Analysis | | | |
|---|---|---|---|---|---|---|
| | | | C | H | N | Cl |
| —$CH_2CH_2Cl$ | 161–162 | Found: | 45.67 | 3.54 | 9.28 | 16.1 |
| | | Calc'd: | 46.37 | 3.46 | 9.0 | 15.21 |
| —$(CH_2)_5CH_3$ | 95–97 | Found: | 54.03 | 5.17 | 8.61 | 7.37 |
| | | Calc'd: | 54.16 | 5.16 | 8.61 | 7.27 |
| —$C_2H_5$ | 156–158 | Found: | 50.13 | 3.99 | 9.70 | 8.34 |
| | | Calc'd: | 50.07 | 3.97 | 9.73 | 8.21 |
| —$(CH_2)_3CH_3$ | 126–127 | Found: | 52.20 | 4.66 | 9.24 | 7.94 |
| | | Calc'd: | 52.23 | 4.60 | 9.13 | 7.71 |

The compounds utilized in the method of the present invention provide selective control of grassy weeds in the presence of valuable crops and give particular and advantageous selective postemergent control of *Echinochloa crusgalli* (commonly known as barnyardgrass or watergrass) in the presence of rice.

For such uses, unmodified active ingredients of the present invention can be employed. However, the present invention embraces the use of the compounds in composition from with an inert material known in the art as an agricultural adjuvant or carrier in solid or liquid form. Thus, for example, an active ingredient can be dispersed on a finely-divided solid and employed therein as a dust or granule. Also, the active ingredients, as liquid concentrates or solid compositions comprising one or more of the active ingredients can be dispersed in water, typically with aid of a wetting agent, and the resulting aqueous dispersion employed as a spray. In other procedures, the active ingredients can be employed as a constituent of organic liquid compositions, oil-in-water and water-in-oil emulsions or water dispersions, with or without the addition of wetting, dispersing, or emulsifying agents. Suitable adjuvants of the foregoing type are well known to those skilled in the art.

The concentration of the active ingredients in solid or liquid compositions generally is from about 0.0003 to about 95 percent by weight or more. Concentrations from about 0.05 to about 50 percent by weight are often employed. In compositions to be employed as concentrates, the active ingredient can be present in a concentration from about 5 to about 98 weight percent. The active ingredient compositions can also contain other compatible additaments, for example, phytotoxicants, plant growth regulants and other biologically active compounds used in agriculture.

In further embodiments, the compounds of the present invention or compositions containing the same, can be advantageously employed in combination with one or more additional pesticidal compounds. Such additional pesticidal compounds may be insecticides, nematocides, arthropodicides, herbicides, fungicides or bactericides that are compatible with the compounds of the present invention in the medium selected for application and not antagonistic to the activity of the present compounds. Accordingly, in such embodiments, the pesticidal compound is employed as a supplemental toxicant for the same or for a different pesticidal use or as an additament. The compounds in combination can generally be present in the ratio of from 1 to 100 parts of the compound of the present invention with from 100 to 1 parts of the additional compound(s).

The exact rate to be applied is dependent not only on a specific active ingredient being applied, but also on a particular action desired, the plant species to be modified and the stage of growth thereof as well as the part of the plant to be contacted with the toxic active ingredient. Thus, all of the active ingredients of the present invention and compositions containing the same may not be equally effective at similar concentrations or against the same plant species.

In selective postemergent operations a dosage of about 0.01 to about 20 pounds/acre (0.0112–2.4 kg/hectare) is generally applicable, although not all compounds are equally effective and some weeds are more difficult to control. Thus, a dosage rate in the range of about 0.05 to about 1.0 pound/acre (0.056–1.12 kg/hectare) is preferred in postemergent control of annual grassy weeds, while about 0.5 to about 5 pounds/acre (0.56–5.6 kg/hectare) is a preferred dosage range for the postemergent control of perennial grassy weeds.

The following examples illustrate effects of the compounds of this invention.

EXAMPLE III

In representative operations, each compound to be utilized in a series of tests was dissolved in acetone to one-half of the final volume (twice the final concentration) to be used and the acetone solution in each case was admixed with an equal volume of water containing 0.1 percent by weight of surface active material. The compositions, generally in the nature of an emulsion, were employed to spray separate respective plant species which had been grown to a height of 2–6 inches in soil of good nutrient content in a greenhouse. Sufficient amounts were employed to provide various application rates as listed in the table. The various beds were positioned side by side and exposed to substantially identical conditions of temperature and light. Each bed was maintained so as to prevent any interaction with test compounds in different seed beds. Other portions of the plants were left untreated to serve as controls. After treatment, the plants were maintained for about two weeks under greenhouse conditions conducive for good plant growth and watered as necessary. The specific plant specie, test compound and dosage and the percent postemergent control obtained are set forth in the table below. Control refers to the reduction in growth compared to the observed results of the same untreated specie. Note that "NT" means "not tested".

Plant species in these tests were the following:

| Common Name | Scientific Name |
|---|---|
| Rice | *Oryza sativa* |
| Barnyardgrass (Watergrass) | *Echinochloa crusgalli* |
| Crabgrass | *Digitaria sanquinalis* |
| Yellow foxtail | *Setaria lutescens* |
| Johnson grass | *Sorghum halepense* |
| Wild oats | *Avena satua* |

POSTEMERGENT CONTROL OF PLANT SPECIES

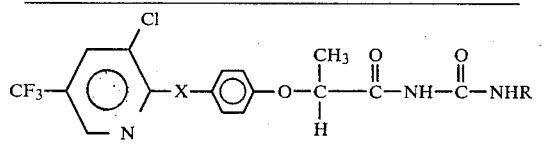

| | | Percent control of indicated dosage rates (ppm) | | | | | |
|---|---|---|---|---|---|---|---|
| R | Plant Species | 250 | 125 | 62.5 | 31.25 | 15.6 | 7.8 |
| —$(CH_2)_3CH_3$ | Barnyard | 100 | 100 | 100 | 0 | 0 | 0 |

POSTEMERGENT CONTROL OF PLANT SPECIES -continued

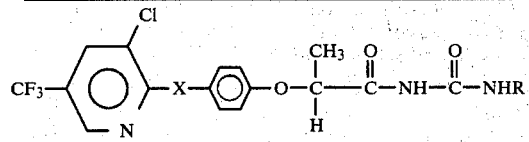

| R | Plant Species | \multicolumn{6}{c}{Percent control of indicated dosage rates (ppm)} |
|---|---|---|---|---|---|---|---|
| | | 250 | 125 | 62.5 | 31.25 | 15.6 | 7.8 |
| | grass | | | | | | |
| | Crabgrass | 100 | 100 | 100 | 80 | 40 | 0 |
| | Foxtail | 100 | 100 | 100 | 0 | 0 | 0 |
| | Johnson grass | 100 | 100 | 100 | 99 | 80 | 0 |
| | Wild oats | 95 | 95 | 70 | 0 | 0 | 0 |
| —C$_2$H$_5$ | Barnyard grass | 100 | 100 | 100 | 100 | 100 | 0 |
| | Crabgrass | 100 | 100 | 100 | 100 | 99 | 40 |
| | Foxtail | 100 | 100 | 100 | 90 | 90 | 0 |
| | Johnson grass | 100 | 100 | 100 | 100 | 90 | 0 |
| | Wild oats | 50 | 100 | 30 | 20 | 0 | 0 |
| —C(CH$_3$)$_2$ | Barnyard grass | 100 | 100 | 100 | 100 | 60 | 0 |
| | | 100 | 99 | 99 | 85 | 80 | 20 |
| | Crabgrass | 100 | 100 | 100 | 70 | 0 | NT |
| | Foxtail | 100 | 100 | 100 | 80 | 90 | 0 |
| | Johnson grass | 100 | 100 | 80 | 20 | 0 | NT |
| | Wild oats | | | | | | |
| —CH$_2$CH$_2$Cl | Barnyard grass | 100 | 100 | 100 | 30 | 0 | NT |
| | Crabgrass | 100 | 100 | 100 | 80 | 60 | 0 |
| | Foxtail | 100 | 100 | 100 | 30 | 0 | NT |
| | Johnson grass | 50 | 40 | 20 | 0 | NT | NT |
| | Wild oats | 60 | 35 | 45 | 0 | 30 | 0 |
| —C$_6$H$_{13}$ | Barnyard grass | 100 | NT | 40 | 0 | NT | NT |
| | Crabgrass | 100 | 100 | 95 | 95 | 95 | 30 |
| | Foxtail | 100 | 100 | 20 | 0 | NT | NT |
| | Johnson grass | 100 | 100 | 100 | 100 | 0 | NT |
| | Wild oats | 100 | 50 | 0 | NT | NT | NT |

EXAMPLE IV

In further representative operations, each compound to be utilized in a series of tests was dissolved in acetone to ½ the final volume (twice the final concentration) to be used and the acetone solution in each case was admixed with an equal volume of water containing 0.1 percent by weight of surface active material. The compositions, generally in the nature of an emulsion, were employed to treat separate respective seed beds of sandy loam soil of good nutrient content wherein each seed bed contained separate groups of viable seeds, each group being of one plane specie. The various beds were positioned side by side and exposed to substantially identical conditions of temperature and light. Each bed was maintained so as to prevent any interaction with test compounds in different seed beds. Each seed bed was treated with one of the compositions as a soil drench applied uniformly throughout the surface of the bed. The compositions were applied to the seed beds so that different seed beds of a given plant specie were treated with one of each of the test compounds. Another seed bed was treated only with water to serve as a control. After treatment, the seed beds were maintained for two weeds under greenhouse conditions conducive for good plant growth and watered as necessary. The specific plant specie, test compound and dosage and the percent preemergent control obtained are set forth in the table below. Control refers to the reduction in growth compared to the observed results of the same specie.

PREEMERGENT CONTROL OF PLANT SPECIES

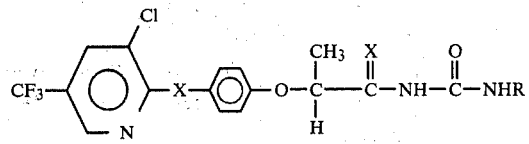

| R | Plant Species | \multicolumn{5}{c}{Percent control at indicated dosage rates (lbs/acre)} |
|---|---|---|---|---|---|---|
| | | 0.5 | 0.25 | 0.125 | 0.063 | 0.032 |
| —(CH$_2$)$_3$CH$_3$ | Barnyard grass | 100 | 100 | 100 | 40 | 20 |
| | Crabgrass | 100 | 100 | 100 | 95 | 90 |
| | Foxtail | 100 | 100 | 100 | 75 | 20 |
| | Johnson grass | 100 | 100 | 100 | 35 | 20 |
| | Wild oats | 100 | 100 | 80 | 50 | 0 |
| —C$_2$H$_5$ | Barnyard grass | 100 | 100 | 100 | 20 | 0 |
| | Crabgrass | 100 | 100 | 100 | 100 | 75 |
| | Foxtail | 100 | 100 | 100 | 45 | 10 |
| | Johnson grass | 100 | 100 | 100 | 45 | 20 |
| | Wild oats | 100 | 85 | 100 | 30 | 0 |
| —CH(CH$_3$)$_2$ | Barnyard grass | 100 | 100 | 95 | 90 | 0 |
| | Crabgrass | 100 | 100 | 100 | 100 | 80 |
| | Foxtail | 100 | 100 | 100 | 80 | 20 |
| | Johnson grass | 100 | 100 | 100 | 60 | 0 |
| | Wild Oats | 100 | 100 | 75 | 10 | 0 |
| —C$_6$H$_{13}$ | Barnyard grass | 60 | 30 | 20 | 10 | 0 |
| | Crabgrass | 100 | 100 | 100 | 100 | 70 |
| | Foxtail | 100 | 100 | 100 | 90 | 0 |
| | Johnson grass | 100 | 100 | 70 | 50 | 0 |
| | Wild oats | 0 | NT | NT | NT | NT |

The compounds of this case exist with an optically active center,

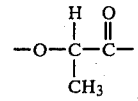

Enantiomorphs often show the same biological effect but to a very different degree. A general discussion of this phenomenon may be found in A. Albert, *Selective Toxicity*, 4th Ed. Met Luen & Co., Ltd., London, 1968, pp. 387–390 and more particular discussions in A. Fredga and B. Aberg, "Stereoisomerism" in plant growth regulators of the auxin type:, *Ann. Rev. Plant Physiology* 16:53–72, 1965 and in E. J. Lien, J. F. R. DeMiranda and E. J. Airens, "Quantitative structure-activity correlation of optical isomers," Molecular Pharmacology 12:598–604, 1976. The finding that the D-enantiomers of substituted phenoxypropionates were twice as active as grass control herbicides as the L-form (DT 2623558) suggests that the D-enantiomers of the present case should also be the more active of the enantiomorphs.

I claim:

1. A compound having the formula

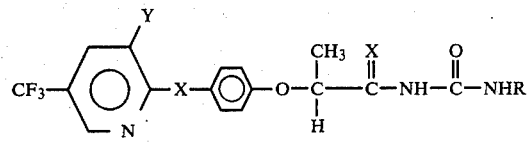

wherein Y is hydrogen, chloro or bromo; X is O or S, and R is an alkyl or chlorosubstituted alkyl radical having from 1 to 6 carbon atoms.

2. Compound of claim 1 which is 2-(4-((3-chloro-5-(trifluoromethyl)-2-pyridyl)oxy)phenoxy)-N-((ethylamino)carbonyl)propanamide.

3. Compound of claim 1 which is N-((butylamino)carbonyl)-2-(4-((3-chloro-5-(trifluoromethyl)-2-pyridyl)oxy)phenoxy)propanamide.

4. A herbicidal composition consisting essentially of a herbicidally effective amount of a compound having the formula

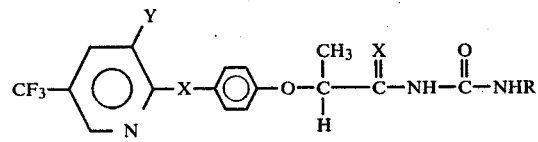

wherein Y is hydrogen, chloro or bromo; X is O or S, and R is an alkyl or chlorosubstituted alkyl radical having from 1 to 6 carbon atoms in admixture with an inert adjuvant therefor.

5. Composition of claim 4 wherein the compound is 2-(4-((3-chloro-5-(trifluoromethyl)-2-pyridyl)oxy)phenoxy)-N-((ethylamino)carbonyl)propanamide.

6. Composition of claim 4 wherein the compound is N-((butylamino)carbonyl)-2-(4-((3-chloro-5-(trifluoromethyl)-2-pyridyl)oxy)phenoxy)propanamide.

7. A method for controlling undesired plant growth which consists essentially of applying a herbicidally effective amount of a compound having the formula

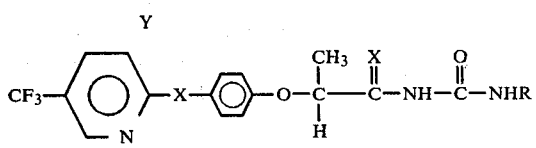

wherein Y is hydrogen, chloro or bromo; X is O or S, and R is an alkyl or chlorosubstituted alkyl radical having from 1 to 6 carbon atoms in admixture with an inert adjuvant therefor.

8. Method of claim 7 wherein the compound is 2-(4-((3-chloro-5-(trifluoromethyl)-2-pyridyl)oxy)phenoxy)-N-((ethylamino)carbonyl)propanamide.

9. Method of claim 7 wherein the compound is N-((butylamino)carbonyl)-2-(4-((3-chloro-5-(trifluoromethyl)-2-pyridyl)oxy)phenoxy)propanamide.

* * * * *